US009128021B2

(12) United States Patent
Oh et al.

(10) Patent No.: US 9,128,021 B2
(45) Date of Patent: Sep. 8, 2015

(54) HOLDER FOR MEASURING PERMEABILITY OF UNCONSOLIDATED SEDIMENT

(71) Applicant: KOREA INSTITUTE OF GEOSCIENCE AND MINERAL RESOURCES, Daejeon (KR)

(72) Inventors: Jun-Ho Oh, Daejeon (KR); Kue-Young Kim, Daejeon (KR); Tae-Hee Kim, Daejeon (KR)

(73) Assignee: Korea Institute of Geoscience and Mineral Resources, Yuseong-Gu (KR)

( * ) Notice: Subject to any disclaimer, the term of this patent is extended or adjusted under 35 U.S.C. 154(b) by 61 days.

(21) Appl. No.: 13/657,697

(22) Filed: Oct. 22, 2012

(65) Prior Publication Data
US 2013/0104629 A1    May 2, 2013

(30) Foreign Application Priority Data
Oct. 31, 2011  (KR) .................. 10-2011-0112132

(51) Int. Cl.
*G01N 15/08*    (2006.01)
*G01N 33/24*    (2006.01)

(52) U.S. Cl.
CPC ........ *G01N 15/0806* (2013.01); *G01N 15/0826* (2013.01); *G01N 33/24* (2013.01)

(58) Field of Classification Search
CPC .............. G01N 15/0826; G01N 15/08; A61K 2300/00; A61K 45/06; C09K 8/512
USPC ........ 73/38, 1.71, 61.65, 23.29, 28.23, 24.04, 73/716, 736, 49.01, 49.05
See application file for complete search history.

(56) References Cited

U.S. PATENT DOCUMENTS

| | | | |
|---|---|---|---|
| 4,555,934 A | | 12/1985 | Freeman et al. |
| 4,679,422 A | * | 7/1987 | Rubin et al. ...................... 73/38 |
| 4,773,264 A | * | 9/1988 | Herron ....................... 73/152.05 |
| 4,966,498 A | * | 10/1990 | Blum ............................ 405/233 |
| 5,105,154 A | * | 4/1992 | Givens et al. .................. 324/376 |
| 5,209,104 A | * | 5/1993 | Collins et al. ..................... 73/38 |
| 5,263,360 A | | 11/1993 | Blauch et al. |
| 5,297,420 A | * | 3/1994 | Gilliland et al. .................. 73/38 |
| 5,363,692 A | * | 11/1994 | Lafargue et al. .................. 73/38 |
| 5,610,322 A | * | 3/1997 | Unger et al. ................. 73/23.39 |
| 5,637,796 A | | 6/1997 | Deruyter et al. |
| 6,425,713 B2 | * | 7/2002 | Fox et al. ...................... 405/243 |
| 6,668,554 B1 | * | 12/2003 | Brown ........................ 60/641.2 |

(Continued)

FOREIGN PATENT DOCUMENTS

JP  08-247910  9/1996
KR  2003-0077055  10/2003

*Primary Examiner* — Peter Macchiarolo
*Assistant Examiner* — Mohammed Keramet-Amircola
(74) *Attorney, Agent, or Firm* — Christie, Parker & Hale, LLP

(57) ABSTRACT

Disclosed is a holder for measuring a permeability of an unconsolidated sediment. The holder includes a sediment installation part having a solid sediment attached to opposite ends of an unconsolidated sediment along a longitudinal direction; a transverse pressure supply part installed to surround the sediment installation part to supply a predetermined transverse pressure to the sediment installation part by using a fluid supplied from the outside; and a longitudinal pressure supply part installed at opposite ends of the transverse pressure supply part to cover opposite ends of the sediment installation part to be moved along a vertical direction so as to supply a predetermined longitudinal pressure to the sediment installation part.

3 Claims, 6 Drawing Sheets

(56) References Cited

U.S. PATENT DOCUMENTS

| | | |
|---|---|---|
| 7,320,221 B2* | 1/2008 | Bronicki ................. 60/641.2 |
| 7,370,574 B2* | 5/2008 | Verna et al. ................. 100/48 |
| 2005/0067162 A1* | 3/2005 | Gjedrem ................. 166/277 |
| 2005/0087018 A1* | 4/2005 | Zamfes ................. 73/601 |
| 2009/0126462 A1* | 5/2009 | Fleury et al. ................. 73/38 |
| 2012/0001429 A1* | 1/2012 | Saar et al. ................. 290/52 |
| 2013/0043678 A1* | 2/2013 | Saar et al. ................. 290/2 |

* cited by examiner

HOLDER FOR MEASURING PERMEABILITY OF UNCONSOLIDATED SEDIMENT

CROSS-REFERENCE TO RELATED APPLICATION

This application claims the benefit under 35 U.S.C. §119 of Korean Patent Application No. 10-2011-0112132 filed on Oct. 31, 2011 in the Korean Intellectual Property Office, the entirety of which disclosure is incorporated herein by reference.

BACKGROUND OF THE INVENTION

1. Field of the Invention

The present invention relates to a holder for measuring a permeability of an unconsolidated sediment, and more particularly to a holder for measuring a permeability of an unconsolidated sediment, which can prevent deformation of the unconsolidated sediment and clogging.

2. Description of the Related Art

In general, a mesh is used on one surface of an unconsolidated core to measure a permeability of an unconsolidated sediment.

An apparatus for measuring a permeability of an unconsolidated sediment according to the related art includes a sleeve surrounding an unconsolidated sediment, and end plugs closely adhering to opposite ends of the unconsolidated sediment.

A gas is injected through an end of the end plug on one side and is discharged through the end plug on the other side.

Thus, according to the related art, a differential pressure of a gas having passed through the unconsolidated sediment.

According to the related art, a longitudinal pressure is applied to the unconsolidated sediment through the end plugs.

Then, when the longitudinal pressure is a predetermined value or higher, the shape of the unconsolidated sediment is deformed.

If the shape of the unconsolidated sediment is deformed, a portion of the deformed sediment may block a gas injection pipe and a gas discharge pipe formed in the end plugs, respectively.

Accordingly, the apparatus according to the related art cannot accurately measure a permeability of the unconsolidated sediment.

Patent documents related to the present invention include Korean Unexamined Patent Application Publication No. 2003-0077055, which discloses a core fixing apparatus including end plugs for pressing an unconsolidated sediment.

SUMMARY OF THE INVENTION

Accordingly, the present invention has been made keeping in mind the above problems occurring in the prior art, and an object of the present invention is to provide a holder for measuring a permeability of an unconsolidated sediment, which can prevent deformation of the unconsolidated sediment under a predetermined test condition.

It is another object of the present invention to provide a holder for measuring a permeability of an unconsolidated sediment, which can prevent dogging of an injection line of an end plug caused by deformation of the unconsolidated sediment It is still another object of the present invention to provide a holder for measuring a permeability of an unconsolidated sediment, which can solve deformation of the unconsolidated sediment, thereby accurately measuring permeability.

The present invention provides a holder for measuring a permeability of an unconsolidated sediment.

According to an aspect of the present invention, there is provided a holder for measuring a permeability of an unconsolidated sediment, the holder including a sediment installation part having a solid sediment attached to opposite ends of an unconsolidated sediment along a longitudinal direction; a transverse pressure supply part installed to surround the sediment installation part to supply a predetermined transverse pressure to the sediment installation part by using a fluid supplied from an outside; and a longitudinal pressure supply part installed at opposite ends of the transverse pressure supply part to cover opposite ends of the sediment installation part and moved along a vertical direction so as to supply a predetermined longitudinal pressure to the sediment installation part.

Preferably, the transverse pressure supply part includes an outer pipe spaced apart from an outer periphery of the sleeve by a predetermined gap and surrounding the sleeve, a fluid introduction part formed at one side of the outer pipe and into which a fluid is introduced from the outside, and a fluid control part formed at an opposite side of the outer pipe to control a hydraulic pressure of the introduced fluid with a predetermined hydraulic pressure.

Preferably, the fluid control part includes a fluid discharge pipe communicated with the opposite side of the outer pipe, a control valve installed in the fluid discharge pipe, a hydraulic pressure measuring unit for measuring the hydraulic pressure, and a control unit for receiving the measured hydraulic pressure and regulating an opening/closing operation of the control valve to maintain a preset reference hydraulic pressure.

Preferably, the longitudinal pressure supply part includes an upper end fixing part installed at an upper end of the outer pipe such that one end of the upper end plug is fixed thereto and a lower end fixing part installed at a lower end of the outer pipe such that one end of the lower end plug is fixed thereto.

At least one of the upper end fixing part and the lower end fixing part may be screw-coupled to the outer pipe.

At least one of the upper end fixing part and the lower end fixing part may form the longitudinal pressure by using the fluid supplied from the outside.

The upper end fixing part may form the longitudinal pressure by using the fluid supplied from the outside, and the lower end fixing part is screw-coupled to a lower end of the outer pipe to form the longitudinal pressure.

The present invention can prevent deformation of the unconsolidated sediment under a predetermined test condition.

The present invention can prevent clogging of an injection line of an end plug due to deformation of the unconsolidated sediment The present invention can solve deformation of the unconsolidated sediment, thereby accurately measuring the permeability.

DETAILED DESCRIPTION OF THE INVENTION

Hereinafter, a holder for measuring a permeability of an unconsolidated sediment according to the present invention will be described with reference to the accompanying drawings.

Figure 1:
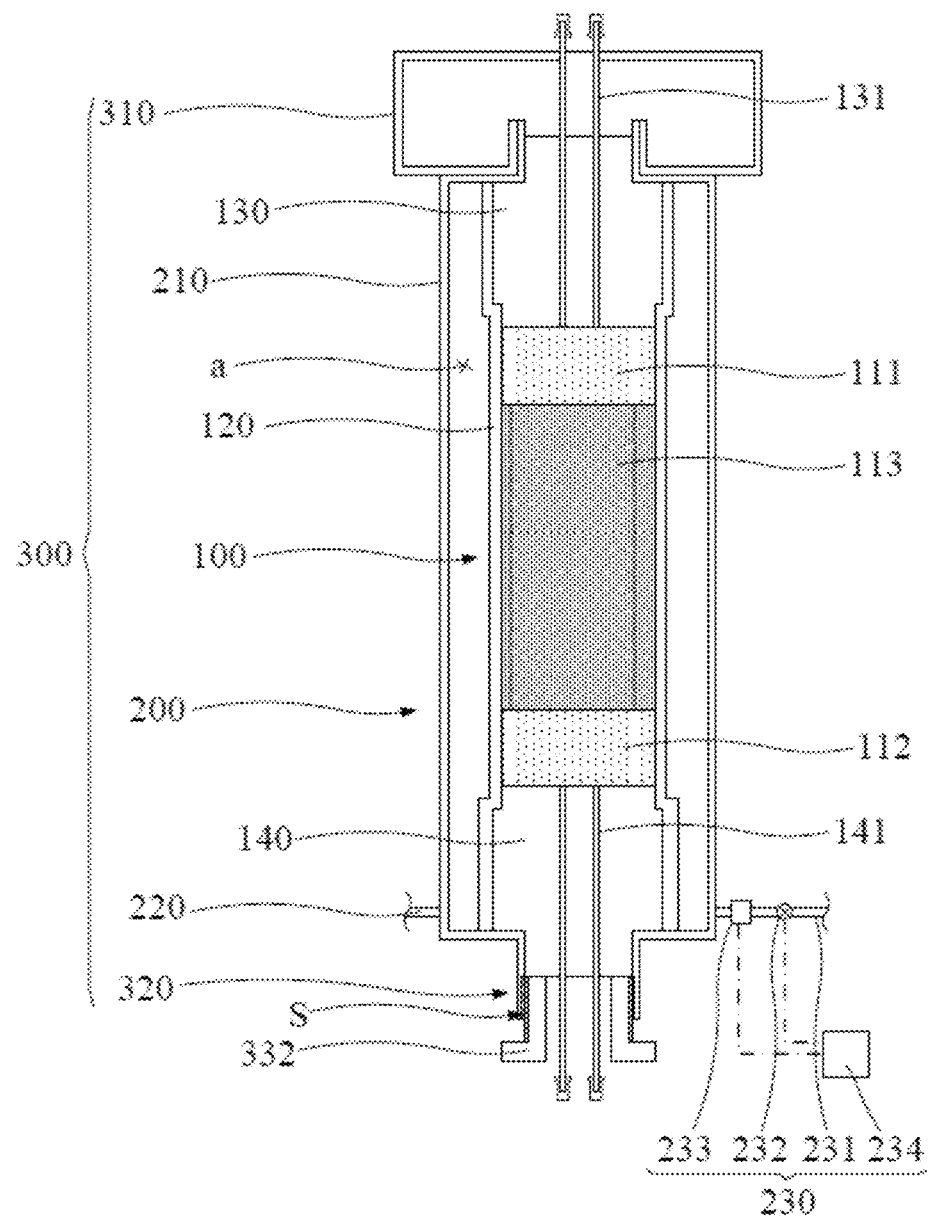
FIG. 1 is a sectional view illustrating a coupled state of a holder for measuring a permeability of an unconsolidated sediment according to the present invention.
Figure 2:
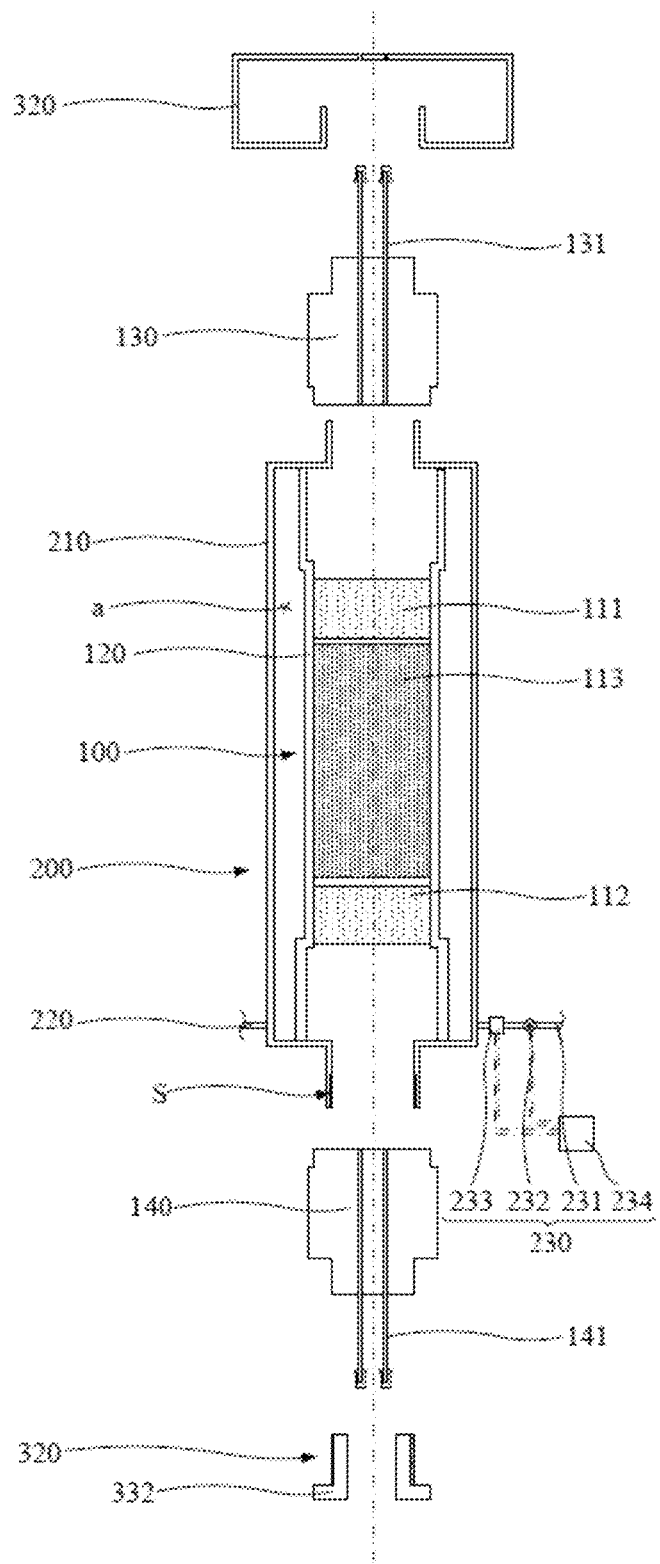
FIG. 2 is an exploded sectional view illustrating the holder for measuring a permeability of an unconsolidated sediment according to the present invention.

FIGS. 1 and 2 are views illustrating a coupled state of a holder for measuring a permeability of an unconsolidated sediment according to the present invention.

Referring to FIGS. 1 and 2, the holder for measuring a permeability of an unconsolidated sediment largely includes a sediment installing part 100, a transverse pressure supply part 200, and a longitudinal pressure supply part 300.

The sediment installing part 100 includes a sleeve 120, a sediment part 110 installed within the sleeve 120, and a pair of end plugs 130 and 140.

The sleeve 120 is formed of a flexible material. The flexible material may be a rubber.

As the sleeve 120 is formed of the flexible material, the sediment part 110 is easily exposed to a pressing condition from the outside.

Opposite ends of the sleeve 120 are opened.

An installation space for installing the sediment part 110 is formed within the sleeve 120.

The sediment part 110 includes an unconsolidated sediment 113, and a pair of solid sediments 111 and 112.

The unconsolidated sediment 113 is a sediment for substantially measuring permeability. The unconsolidated sediment has a first length L1.

The pair of solid sediments 111 and 112 may be a rock sediment having a predetermined permeability.

The pair of solid sediments 111 and 112 have a second length L2.

Here, the second length L2 may be shorter than the first length L2 by a predetermined length.

The pair of solid sediments 111 and 112 and the unconsolidated sediment 113 have the same longitudinal sectional area.

The pair of solid sediments 111 and 112 include first and second solid sediments 111 and 112. The first solid sediment 111 is attached to one end or an upper end of the unconsolidated sediment 113, and the second solid 112 is attached to an opposite end or a lower end of the unconsolidated sediment 113.

Thus, when the sleeve is erected vertically, the first and second solid sediments 111 and 112 are disposed on upper and lower sides with respect to the unconsolidated sediment 113 in the installation space of the sleeve 120, respectively.

The pair of end plugs 130 and 140 includes an upper end plug 130 and a lower end plug 140. The end plugs 130 and 140 may be formed of a stainless material having a corrosion resisting property.

The upper end plate 130 is disposed at an upper end of the sleeve 120.

A lower surface of the upper end plate 130 is attached to an upper surface of the first solid sediment 111.

A pair of gas discharge pipes 131 is installed in the upper end plug 130.

An end of the gas discharge pipe 131 is exposed to a bottom surface of the upper end plug 130, and an opposite end of the gas discharge pipe 131 protrudes from an upper surface of the upper end plug 130.

A pair of gas introduction pipes 141 is installed in the lower end plug 140.

One end of the gas introduction pipe 141 is exposed to an upper surface of the lower end plug 140, and an opposite end of the gas introduction pipe 141 protrudes from a lower surface of the lower end plug 140.

The transverse pressure supply part 200 includes an outer pipe 210, a fluid introduction part 220, and a fluid control part 230.

Upper and lower ends of the outer pipe 210 are opened, and a predetermined space is formed in the outer pipe 210.

The sediment installation part 100 is disposed in an interior space of the outer pipe 210.

Here, an outer surface of the sleeve 120 of the sediment installation part 100 and an inner wall of the interior space of the outer pipe 210 are spaced apart from each other by a predetermined distance.

Thus, a predetermined spacing space is formed between the sleeve 120 and the inner wall of the outer pipe 210. The spacing space is a space a filled with a fluid.

The fluid introduction part 110 is formed at one side of the outer pipe 210. The fluid introduction part 110 has a pipe shape, and is communicated with the fluid space a.

The fluid provided from the outside may be introduced into the fluid space a through the fluid introduction part 110.

The fluid control part 230 is installed at an opposite side of the outer pipe 210.

The fluid control part 230 includes a fluid discharge pipe 231, a check valve 232, a hydraulic pressure measuring unit 233, and a control unit 234.

The fluid discharge pipe 231 is communicated with the fluid space at an opposite side of the outer pipe 210.

The check valve 232 may be installed on the fluid discharge pipe 231. The check valve 232 is an electronic valve for receiving an electric signal from the control unit 234 to open and close the fluid discharge pipe 231.

The hydraulic pressure measuring unit 233 is a unit for measuring a pressure of the fluid filled in the fluid space a.

The hydraulic pressure measuring unit 233 transmits the measured hydraulic pressure to the control unit 234.

The control unit 234 judges whether the transmitted hydraulic pressure is identical with a preset reference hydraulic pressure.

The control unit 234 controls an opening/closing operation of the check valve 232 such that the transmitted hydraulic pressure is identical to the reference hydraulic pressure.

The longitudinal pressure supply part 300 according to the present invention includes an upper end fixing part 310 and a nut part 332. Here, the reference numeral of the nut part 332 is the same as that of a lower end nut part.

The upper end fixing part 310 is installed at an upper end of the outer pipe 210.

The upper end plug 130 is exposed to an interior space of the upper end fixing part 310, in an interior space of the outer pipe 210.

A boss 212 having a screw thread on an inner periphery thereof is formed at a lower end of the outer pipe 210.

The upper end plug 140 is exposed to an inner periphery of the boss 212, in an interior space of the outer pipe 210.

The nut part 332 screw-coupling with the screw thread is installed in the boss 212.

The nut part 332 is elevated along a screw rotation direction,

The nut part 332 contacts a lower surface of the lower end plug 140.

Thus, as the nut part 332 is elevated, the lower end plug 140 may be moved upward and downward.

Next, a method of measuring a permeability using the above-configured holder for measuring a permeability of an unconsolidated segment will be described.

As illustrated in FIGS. 1 and 2, solid sediments 111 and 112 which are rocks are attached to opposite ends of the unconsolidated sediment 113.

The sediment part 110 is installed within the sleeve 120.

The upper end plug 130 is disposed on an upper surface of the first solid sediment 111, and the lower end plug 140 is disposed on a lower surface of the second solid sediment 112.

The sediment installation part 100 is installed in an interior space of the outer pipe 210. The fluid space a is formed between an inner wall of the outer pipe 210 and the sediment installation part 100.

The upper end fixing part 310 is installed at an upper end of the outer pipe 210, and a lower end fixing part 320 is installed at a lower end of the outer pipe 210.

The nut part 332 for pressing the lower end plug 140 is installed at the lower end fixing part 320.

After the sediment installation part 100 is completely mounted within the outer pipe 210, a transverse pressure and a longitudinal pressure are supplied to the sediment part 110.

When the transverse pressure is supplied, a fluid such as an oil having a predetermined viscosity is supplied into the fluid space a through the fluid introduction part 220.

Accordingly, the sleeve 210 exposed to the fluid space a is pressed by the introduced oil.

Then, the fluid discharge pipe 231 remains closed in the fluid control part 230.

Further, the hydraulic pressure measuring unit 233 measures a pressure of the introduced oil in real time, and transmits the measured pressure to the control unit 234.

If the measured hydraulic pressure reaches a preset reference hydraulic pressure, the control unit 234 doses the check valve 232. Next, the control unit 234 closes the fluid introduction part 220 by using a valve (not illustrated).

Accordingly, a transverse pressure corresponding to a reference inflow is supplied to the sediment installation part 100.

When a longitudinal pressure is supplied, the nut part 332 may be used.

If the nut part 332 is rotated to one side, for example, along a direction where the nut part 332 is coupled to the boss 212 formed in the lower end fixing part 320, the nut part 332 is elevated.

Then, since the lower end plug 140 contacts an upper surface of the nut part 332, the lower end plug 140 is raised upward in conjunction with the elevation of the nut part 332.

Thus, the sediment part 110 disposed between the upper and lower end plugs 130 and 140 receive a predetermined longitudinal pressure.

Further, as an oil is introduced into an interior space of the upper end fixing part 310 in the way by which the oil is introduced, the upper end plug 130 may be pressed downward.

In the present invention, the transverse pressure and the longitudinal pressure may be applied while maintaining the same value.

In this state, a gas having a predetermined flux is supplied to the sediment part 110 through a gas injection pipe 141.

The gas supplied from the gas injection pipe 141 passes through the sediment part 110 and is discharged through the gas discharge pipe 131.

Figure 4:
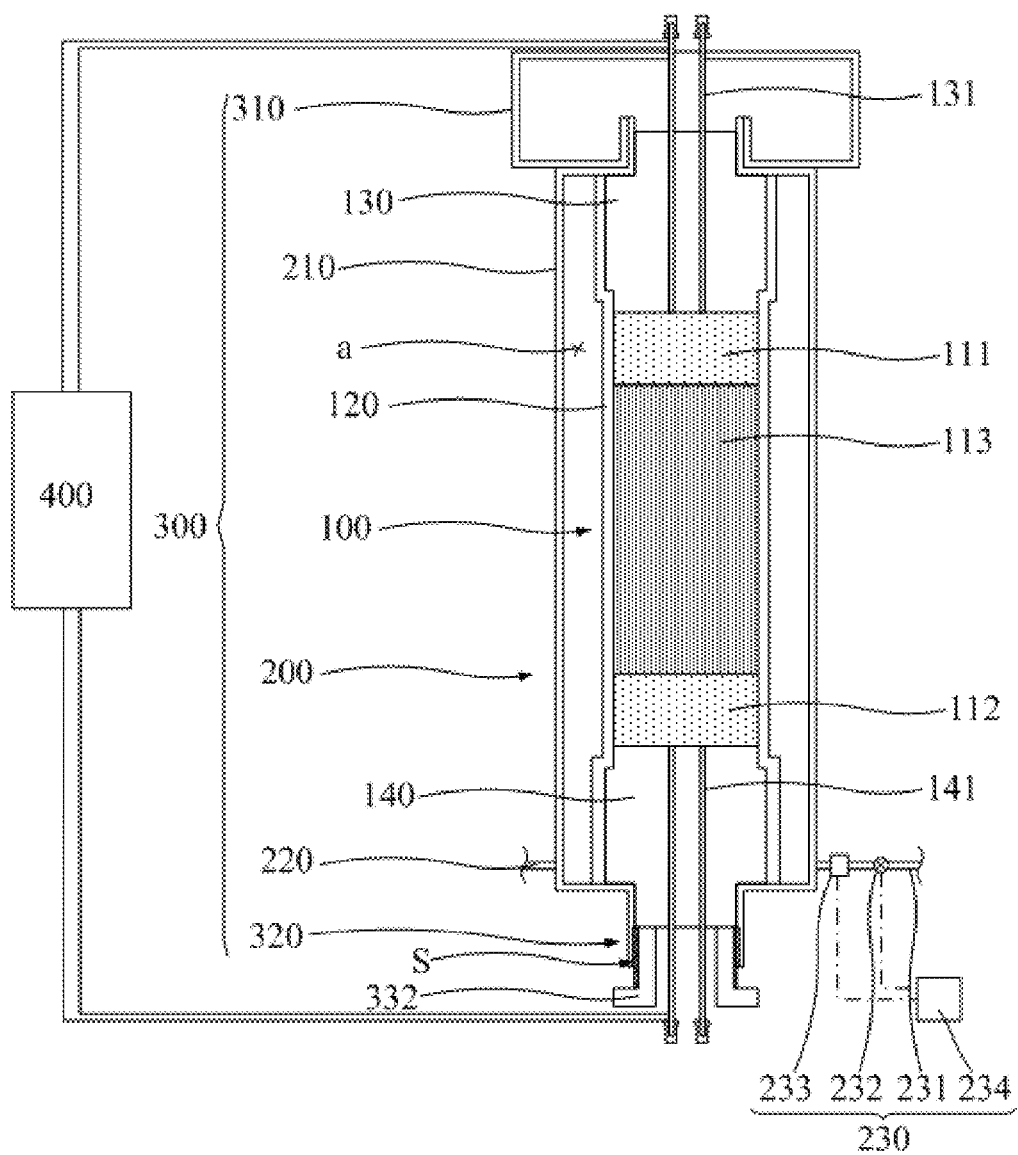
FIG. 4 is a view illustrating an apparatus where the holder for measuring a permeability of an unconsolidated sediment according to the present invention and a differential transducer are installed.

Referring to FIG. 4, the differential transducer 400 is installed between the gas injection pipe 141 and the gas discharge pipe 131.

The differential transducer 400 may calculate a pressure difference between the gas injection pipe 141 and the gas discharge pipe 131 and transmit the calculated pressure difference to the control unit.

Figure 3:
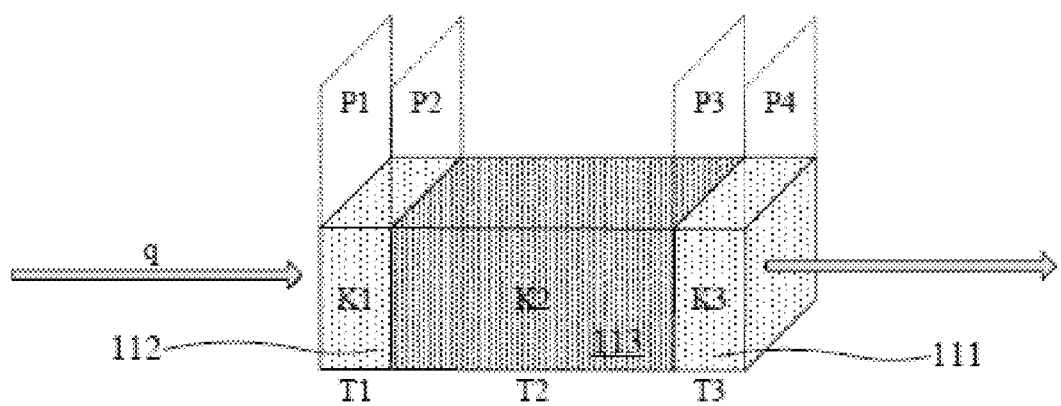
FIG. 3 is a schematic diagram illustrating a flux of a gas passing through a sediment according to the present invention.

FIG. 3 is a view illustrating an example where a gas flows to the sediment part, Referring to FIGS. 1 and 3, a flux of the gas introduced from the gas injection pipe 141 is V.

Further, the second solid sediment 112 has a permeability coefficient of 'k1' and a thickness of 'T1'.

The unconsolidated sediment 113 has a permeability coefficient of 'k2' and a thickness of 'T2'.

The first solid sediment 111 has a permeability coefficient of 'k3' and a thickness of 'T3'.

Here, P1, P2, P3, and P4 are pressures, and A are cross-sections of the sediments 111, 112, and 113. The cross-sections are the same.

Thus, a difference between an initial injection pressure P1 of the gas and a discharge pressure P4 of the gas has a relationship of (P1−P2)+(P2−P3)+(P3−P4).

$$\frac{qT}{KA} = \frac{qT_1}{K_1 A} + \frac{qT_2}{K_2 A} + \frac{qT_3}{K_3 A} \qquad \text{[Equation 1]}$$

Here, since the permeability of the first and second solid sediments 111 and 112 are known, the following Equations 2 and 3 may be satisfied.

$$\frac{T_{total}}{K_{total}} = \frac{T_{known}}{K_{known}} + \frac{T_{unknown}}{K_{unknown}} \qquad \text{[Equation 2]}$$

$$\frac{T_{unknown}}{K_{unknown}} = \frac{T_{total}}{K_{total}} + \frac{T_{known}}{K_{known}} \qquad \text{[Equation 3]}$$

The permeability coefficient of the unconsolidated sediment 113 may be calculated as in the following Equation 4 by using the above equations.

$$K_{unknown} = \frac{T_{unknown}}{\dfrac{T_{total}}{K_{total}} - \dfrac{T_{known}}{K_{known}}} \qquad \text{[Equation 4]}$$

A permeability of the unconsolidated sediment 113 according to the present invention can be measured through the above-described method.

In the embodiment of the present invention, regulation of a transverse pressure through introduction of a gas and regulation of a longitudinal pressure using the nut part may be selectively carried out.

In the embodiment of the present invention, since opposite ends of the unconsolidated sediment may be attached by the rock sediment under a predetermined test pressing condition, the unconsolidated sediment can be prevented from being deformed.

In the embodiment of the present invention, the gas injection pipe of the end plug can be prevented from being blocked due to deformation of the unconsolidated sediment.

In the embodiment of the present invention, permeability can be measured more accurately by solving deformation of the unconsolidated sediment.

Figure 5:
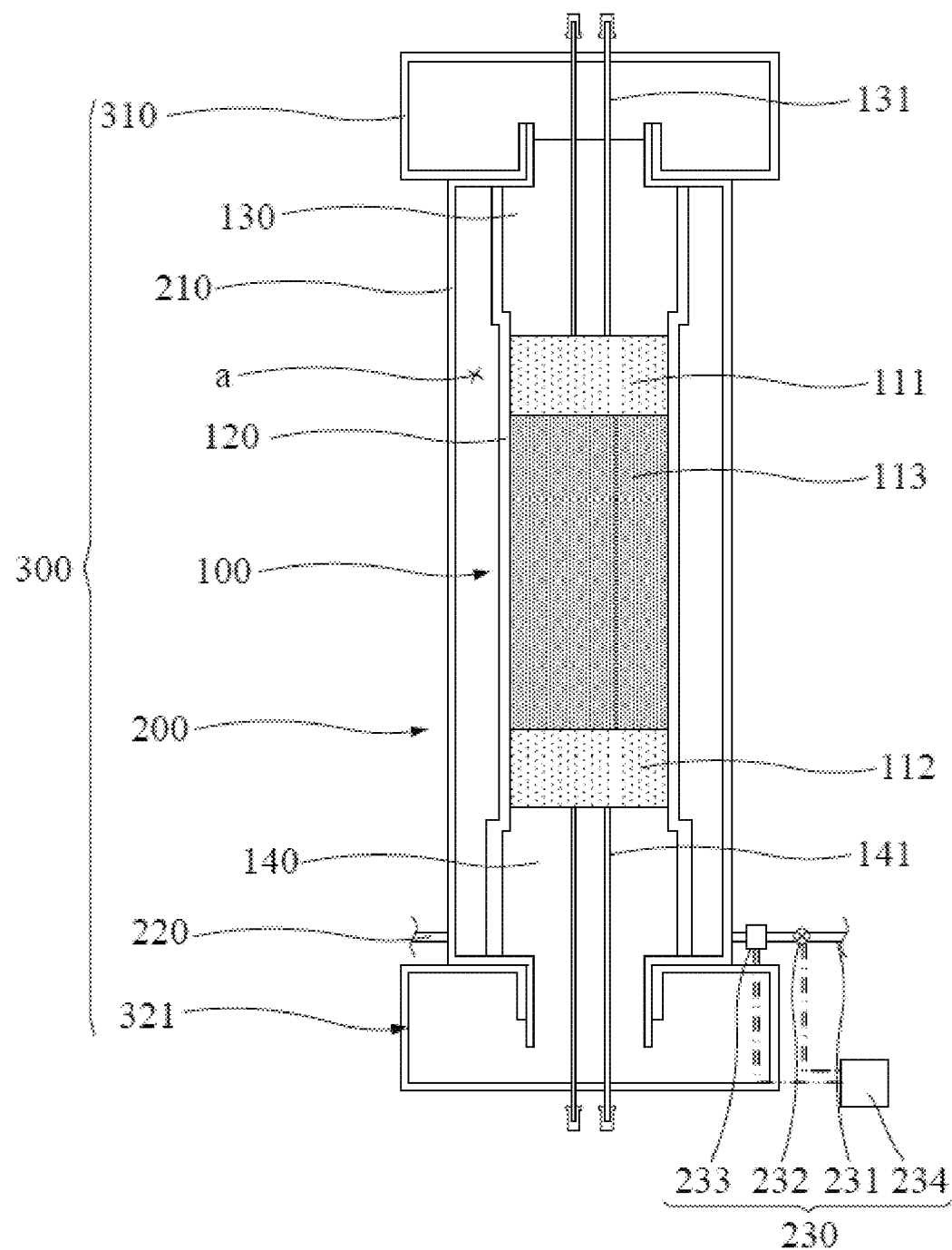
FIG. 5 is a sectional view illustrating another example of a holder for measuring a permeability of an unconsolidated sediment according to the present invention.

FIG. 5 is a sectional view illustrating another example of a holder for measuring a permeability of an unconsolidated sediment according to the present invention.

Referring to FIG. 5, a longitudinal pressure supply part 300 according to the present invention includes an upper end fixing part 310 and a lower end fixing part 321.

One end of the upper end plug 130 is fixed to the upper end fixing part 310, and the upper end fixing part 310 is installed at an upper end of an outer pipe 210.

One end of the lower end plug 140 is fixed to the lower end fixing part 321, and the lower end fixing part 321 is installed at a lower end of an outer pipe 210.

A fluid such as an oil is supplied from the outside to any one of the upper fixing part 310 and the lower fixing part 321.

The upper end fixing part 310 or the lower end fixing part 321 may include a configuration such as a fluid introduction part 220 and a fluid control part 230 which has been described above.

Thus, the fluid supplied to any one of the upper end fixing part 310 and the low end fixing part 321 may form a predetermined pressure.

Accordingly, the upper end plug 130 or the lower end plug 140 may receive a predetermined pressing force along a longitudinal direction.

In the embodiment of the present invention, as the fluid is supplied to any one of the upper end fixing part and the lower end fixing part, at least one of the pair of end plugs may be pressed to supply the longitudinal pressure to the sediment part.

Figure 6:
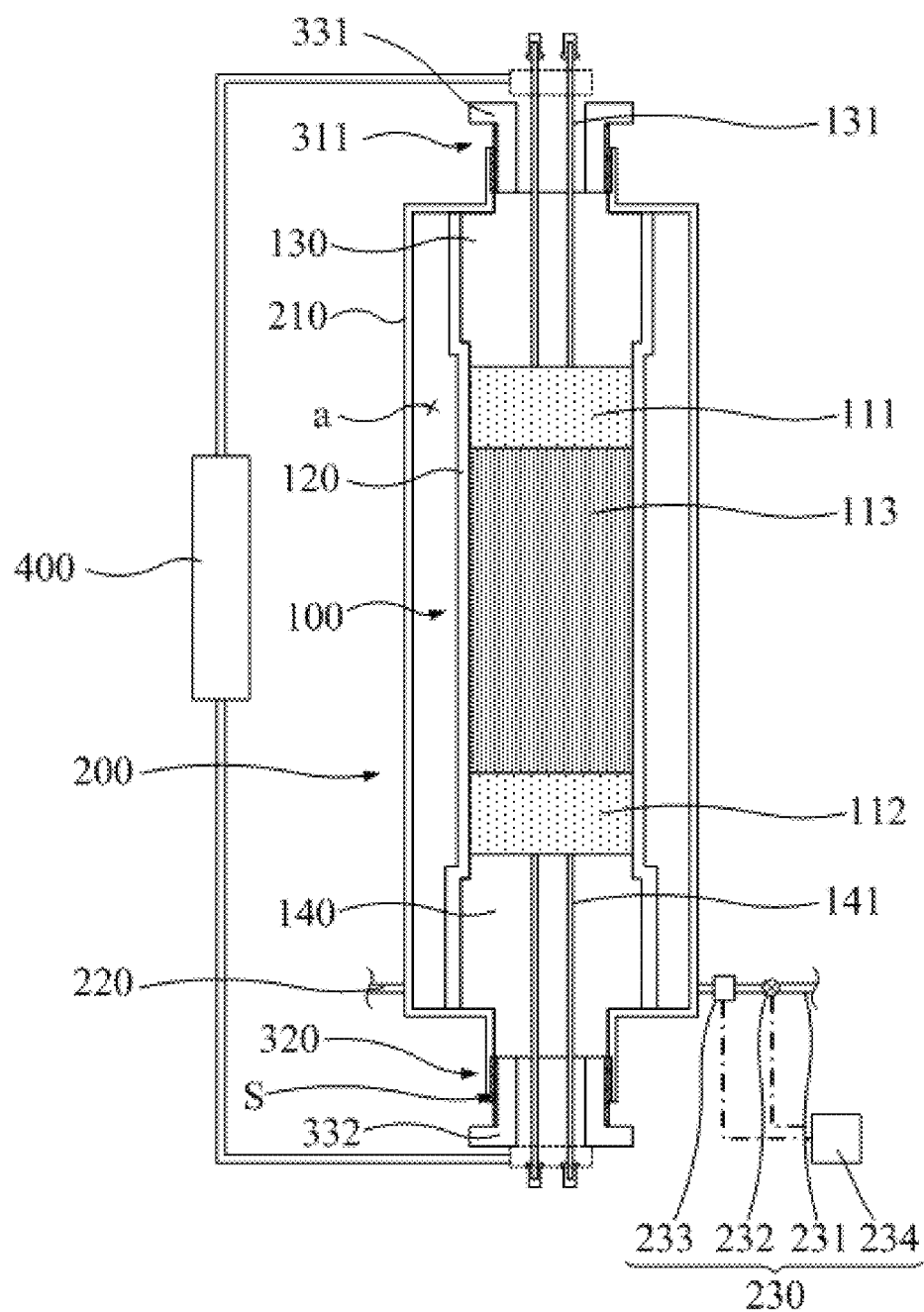
FIG. 6 is a sectional view illustrating another example of a holder for measuring a permeability of an unconsolidated sediment according to the present invention.

FIG. 6 is a sectional view illustrating another example of a holder for measuring a permeability of an unconsolidated sediment according to the present invention.

Referring to FIG. 6, the longitudinal pressure supply part according to the present invention includes an upper end fixing part 311 and a lower end fixing part 320.

One end of the upper end plug 130 is fixed to the upper end fixing part 311, and the upper end fixing part 311 is installed at an upper end of the outer pipe 210.

An upper end protrusion 211 protruding upward is formed at the upper end fixing part 311. A screw thread is formed in an interior of the upper end protrusion 211.

An upper end nut part 331 is installed in the upper end protrusion 211.

One end of the lower end plug 140 is fixed to the lower end fixing part 320, and the lower end fixing part 320 is installed at a lower end of the outer pipe 210.

A lower end protrusion 212 protruding downward is formed at the lower end fixing part 321. A screw thread is formed in an interior of the lower end protrusion 212.

A lower end nut part 332 is installed in the lower end protrusion 212.

The upper end nut part 331 is elevated along a direction in which the upper end nut part 331 is screw-coupled (S) to the upper end protrusion 211. A lower surface of the upper nut part 331 is attached to an upper surface of the upper end plug 130.

The lower end nut part 332 is elevated in a direction in which the lower end nut part 332 is screw-coupled (S) to the lower end protrusion 212. An upper surface of the lower end nut part 332 is attached to a lower surface of the lower end plug 140.

According to the screw-coupling (5) direction of the upper end nut part 331 or the lower end nut part 332, the sediment part 110 in the sediment installation part 100 may receive a predetermined pressing force along a longitudinal direction.

In the embodiment of the present invention, the longitudinal pressure may be supplied to the sediment by pressing at least one of the pair of end plugs.

What is claimed is:

1. A holder for measuring a permeability of an unconsolidated sediment in order to prevent the unconsolidated sediment from being deformed, the holder comprising:
    a sediment installation part having a solid sediment attached to opposite ends of an unconsolidated sediment along a longitudinal direction;
    a transverse pressure supply part installed to surround the sediment installation part to supply a predetermined transverse pressure to the sediment installation part by using a fluid supplied from an outside; and
    a longitudinal pressure supply part installed at opposite ends of the transverse pressure supply part to cover opposite ends of the sediment installation part and moved along a vertical direction so as to supply a predetermined longitudinal pressure to the sediment installation part,
    wherein the fluid is an oil having a predetermined viscosity,
    wherein the sediment installation part comprises:
        a flexible sleeve having open upper and lower ends and formed therein with an installation space where the unconsolidated sediment and the solid sediment are installed;
        an upper end plug installed at an upper end of the sleeve to press the solid sediment provided at an upper side, and having a gas discharge pipe; and
        a lower end plug installed at an upper end of the sleeve to press the solid sediment provided at a lower side, and having a gas injection pipe, and
    wherein the transverse pressure supply part comprises:
        an outer pipe spaced apart from an outer periphery of the sleeve by a predetermined gap and surrounding the sleeve;
        a fluid introduction part formed at one side of the outer pipe and into which a fluid is introduced from the outside; and
        a fluid control part formed at an opposite side of the outer pipe to control a hydraulic pressure of the introduced fluid with a predetermined hydraulic pressure, and
    wherein the longitudinal pressure supply part comprises:
        an upper end fixing part installed at an upper end of the outer pipe such that one end of the upper end plug is fixed thereto; and
        a lower end fixing part installed at a lower end of the outer pipe such that one end of the lower end plug is fixed thereto,
        wherein a nut part is screw-coupled with at least one of the upper fixing part and the lower fixing part to move the upper end plug or the lower end plug in a longitudinal direction.

2. The holder as claimed in claim 1, wherein the solid sediment is a rock sediment having a preset permeability.

3. The holder as claimed in claim 1, wherein the fluid control part includes:
    a fluid discharge pipe communicated with the opposite side of the outer pipe;
    a control valve installed in the fluid discharge pipe;
    a hydraulic pressure measuring unit for measuring the hydraulic pressure; and a control unit for receiving the measured hydraulic pressure and regulating an opening/closing operation of the control valve to maintain a preset reference hydraulic pressure.

* * * * *